(12) United States Patent
Liu et al.

(10) Patent No.: US 8,784,556 B2
(45) Date of Patent: Jul. 22, 2014

(54) ANGLE-DEPENDENT INTERFERENCE PIGMENTS

(75) Inventors: Weizhong Liu, Shantou (CN); Yulin Zhuang, Shantou (CN)

(73) Assignee: Shantou Longhua Pearl Lustre Pigments Co., Ltd., Shantou (CN)

( * ) Notice: Subject to any disclaimer, the term of this patent is extended or adjusted under 35 U.S.C. 154(b) by 405 days.

(21) Appl. No.: 12/994,759

(22) PCT Filed: Feb. 24, 2010

(86) PCT No.: PCT/CN2010/070734
§ 371 (c)(1),
(2), (4) Date: Nov. 25, 2010

(87) PCT Pub. No.: WO2011/103713
PCT Pub. Date: Sep. 1, 2011

(65) Prior Publication Data
US 2011/0306678 A1    Dec. 15, 2011

(51) Int. Cl.
| | | |
|---|---|---|
| C09D 1/00 | (2006.01) |
| C09D 11/00 | (2014.01) |
| C09C 1/28 | (2006.01) |
| C04B 35/628 | (2006.01) |
| A61Q 19/00 | (2006.01) |
| C03C 17/34 | (2006.01) |
| C09D 5/36 | (2006.01) |
| C09C 1/00 | (2006.01) |
| A61K 8/02 | (2006.01) |
| A61K 8/26 | (2006.01) |
| A61K 8/25 | (2006.01) |
| A61K 8/29 | (2006.01) |
| C09D 7/12 | (2006.01) |

(52) U.S. Cl.
CPC ....... *C03C 17/3417* (2013.01); *C04B 35/62886* (2013.01); *C04B 35/62813* (2013.01); *A61Q 19/00* (2013.01); *C09C 2200/102* (2013.01); *C01P 2002/85* (2013.01); *C04B 2235/5436* (2013.01); *A61K 2800/10* (2013.01); *C09C 2200/302* (2013.01); *C09D 5/36* (2013.01); *C09C 1/0039* (2013.01); *A61K 8/0266* (2013.01); *C04B 35/62821* (2013.01); *C09C 2200/303* (2013.01); *C09C 1/0024* (2013.01); *C04B 2235/3454* (2013.01); *C04B 2235/9661* (2013.01); *C09C 2200/401* (2013.01); *C04B 35/62807* (2013.01); *C03C 2217/734* (2013.01); *C04B 35/62826* (2013.01); *C04B 2235/36* (2013.01); *A61K 8/26* (2013.01); *A61K 2800/436* (2013.01); *A61K 8/25* (2013.01); *C04B 35/62894* (2013.01); *C04B 2235/5292* (2013.01); *A61K 8/29* (2013.01); *C04B 35/6281* (2013.01); *C04B 2235/3481* (2013.01); *C09D 7/1225* (2013.01); *C01P 2004/03* (2013.01)
USPC ............................ 106/481; 106/446; 106/456

(58) Field of Classification Search
USPC ......... 106/415, 417–418, 436, 439, 442, 456, 106/457, 481
See application file for complete search history.

(56) References Cited

U.S. PATENT DOCUMENTS 6,596,070 B1 *   7/2003   Schmidt et al. ............... 106/417

* cited by examiner

*Primary Examiner* — Pegah Parvini

(57) ABSTRACT

An angle-dependent interference pigment based on transparent or translucent inorganic flake serving as a substrate is provided. The substrate is coated by coatings (A)+(B)+(C) and optionally coating (D), so as to form a "high-low-high" refractive index layered structure. The coatings (A) and (C) consist of metal oxides, silicate, aluminates and/or a mixture thereof. The coating (B) consist of silicon oxide, hydrous silicon oxide, aluminum oxide, hydrous aluminum oxide, magnesium oxide, hydrous magnesium oxide and/or a mixture thereof. The angle-dependent interference pigments have high color saturation in the transitional region and a significantly gradual color change in the color changing region. The present pigments can be used as colored coatings, including printing ink, or can be used in the preparation of plastics, glass, ceramics and the like. The pigment of the present invention is particularly used in the cosmetic industry which has a very high requirement on gradual color change.

12 Claims, 3 Drawing Sheets

US 8,784,556 B2

ANGLE-DEPENDENT INTERFERENCE PIGMENTS

FIELD OF THE INVENTION

The present invention relates to pigments, particularly to interference pigments based on multi-coated flakes, and more specifically to angle-dependent interference pigments with high color saturation and significant angle-dependence performance.

BACKGROUND OF THE INVENTION

Multilayer pigments alternately coated with layers having high and low refractive index are known in the art. The optical effect of the pigments depends on the material of flakes, the material and thickness of respective layers, and the manufacturing methods for the pigments. Angle-dependent interference pigments exhibit two or more interference colors when observed from different viewing angles. For pigments having inorganic material flake that is coated with alternating layers of metal oxides and nonmetal oxides, due to the significant difference between the refractive indices of the metal oxides layers and the nonmetal oxide layers, there is a sudden change of refractive index at the interface between the layers with high refractive index and the layers with low refractive index, which likely causing disadvantages such as poor color saturation in the transitional region of the pigments and no significant color change in the color changing region, thus limiting the application of the pigments in cosmetics and automobile finish.

SUMMARY OF THE INVENTION

An object of the present invention is to provide an angle-dependent interference pigments having high color saturation and significant angle-dependence performance.

In order to achieve the above-mentioned object, there is provide an angle-dependent interference pigment based on transparent or translucent inorganic flake serving as a substrate, the substrate being coated by at least one layer packet comprising in sequence by:
  (A) a coating having high refractive index,
  (B) a colorless coating having a refractive index $n \leq 1.8$,
  (C) a coating having high refractive index, and
  (D) optionally, an outer protective layer;
wherein the coating (B) is always between coating (A) and coating (C) so as to form a "high-low-high" refractive index layered structure, the "high-low-high" refractive index layered structure having an odd number of layers with the odd number being 3 or more; the coatings (A) and (C) consisting of metal oxides, silicate, aluminates and/or a mixture thereof; the coating (B) consisting of silicon oxide, hydrous silicon oxide, aluminum oxide, hydrous aluminum oxide, magnesium oxide, hydrous magnesium oxide and/or a mixture thereof.

Preferably, the coating (B) consisting of silicon oxide or a mixture of silicon oxide and hydrous silicon oxide.

Suitable materials for the coatings (A) and (C) are selected from a group consisting of materials with nonselective optical absorption, such as colorless metal oxides, silicate, aluminates and/or a mixture thereof; and materials with selective optical absorption, such as colored metal oxides, silicate, aluminates and/or a mixture thereof. The coatings (A) and (C) have a gradual change in refractive index. The closer to the interface between coatings (A) and (B) or to the interface between coatings (C) and (B), the lower the refractive index is; the further from the interface between coatings (A) and (B) or from the interface between coatings (C) and (B), the higher the refractive index is.

In particular, the coatings (A) and (C) may consist of colorless and high refractive index titanium dioxide, titanium silicate, titanosilicate and/or a mixture thereof, wherein the contents of silicon and titanium in titanium silicate and titanosilicate vary. The closer to the interface between coatings (A) and (B) or to the interface between coatings (C) and (B), the more the silicon is and the less the titanium is, and in turn the lower the refractive index is; on the other hand, the further from the interface between coatings (A) and (B) or from the interface between coatings (C) and (B), the more the titanium is and, in turn, the higher the refractive index is.

Alternatively, the coatings (A) and (C) may consist of colored and high refractive index ferric oxide, ferric silicate, and/or a mixture thereof, wherein the contents of ferric and silicon in ferric silicate vary. The closer to the interface between coatings (A) and (B) or to the interface between coatings (C) and (B), the more the silicon is and the less the iron is, and in turn the lower the refractive index is; on the other hand, the further from the interface between coatings (A) and (B) or from the interface between coatings (C) and (B), the more the iron is and, in turn, the higher the refractive index is.

The coating (B) with low refractive index may also homogeneously or inhomogeneously contain ferric silicate or titanium silicate.

The interference color variation of the pigments is determined by the thickness of the coating (B). However, the variation region and chromaticity of the color is closely related with the thicknesses of the coatings (A) and (C), in addition to the thickness of the coating (B).

The thickness of the coating (B) is in the range of 20-1000 nm and preferably 50-900 nm.

The thickness of the coatings (A) and (C) is respectively in the range of 5-165 nm and preferably 10-150 nm.

Suitable inorganic flake can be a silicatic platelet consisting essentially of light or white mica and preferably wet ground muscovite mica. The silicatic platelet also can be other natural mica, artificial mica, talcum powder or sheet glass.

The structure of alternate coatings of high refractive index material and transparent or translucent low refractive index material enables the pigments to exhibit a range of interference colors as observed from different viewing angles, which is so called angle-dependent performance.

It is discovered by the inventor that the pigment exhibits, instead of different interference colors, a single interference color such as silvery white, yellow, orange, red, purple, blue or green as the coating rate increases, when only the coating (A), for example consisting of titanium dioxide, is coated on the substrate.

In addition, when the substrate is first coated the coating (A) and followed by coating with the coating (B), the pigment exhibits interference colors when in a form of dry powder and the interference colors disappear when dispersed in varnish.

Moreover, when the substrate is coated the coatings (A) and (B) and followed by coating with the coating (C), the pigment exhibits different interference colors, and when the thicknesses of these three coatings are adjusted to a proper ratio range, a color flow effect can be obtained and the color saturation is also preferably higher.

The pigments of the present invention can also comprise an outer protective layer (D) in order to provide the pigments with weatherability and water resistance, and thus promote outdoor use thereof for example as exterior wall coating or automobile paint.

The protective layer (D) may consist of metal oxides with low refractive index or high refractive index. The metal oxides may be colorless or colored, such as silicon oxide, hydrous silicon oxide, aluminum oxide, hydrous aluminum oxide, tin oxide, zirconium dioxide, chromium(III) oxide, cerium oxide and/or a mixture thereof The protective layer (D) may also consist of a mixture of silicate and oxides.

The protective layer (D) can have a coating weight dependent on the requirements of different application fields.

The final interference color of the pigment may also be affected by the protective layer (D) to some extent. When a colorless metal oxide with low refractive index, such as silicon oxide, hydrous silicon oxide, aluminum oxide, hydrous aluminum oxide, is coated by the protective layer (D), the interference color of the pigment is less affected due to the low refractive index.

On the other hand, when a colored metal oxide such as chromium(III) oxide is coated by the protective layer (D), the apparent color and interference color of the pigment is more or less affected. When a colorless metal oxide with high refractive index such as tin oxide or zirconium dioxide is coated by the layer (D), the interference colors of the pigment may be increased, thus the uses of the pigment should be careful.

In one embodiment, the pigments of the present invention is prepared by wet chemistry method which alternately deposits on the surface of the substrate (i) a mixture layer of high refractive index metal oxides, silicate and aluminates, and (ii) a low refractive index silicon oxide layer or aluminum oxide.

In the angle-dependent interference pigment of the present invention, coatings with high refractive index comprises silicate, aluminates and/or a mixture thereof besides metal oxides, and the silicate, aluminates and/or a mixture thereof have its highest content at the interface between the coating with high refractive index and the coating with low refractive index and less content far from the interface. The silicate and aluminates have a lower refractive index than metal oxides and a higher refractive index than silicon oxide. Therefore, a structure with gradually and homogeneously varied refractive index can be obtained. The angle-dependent interference pigments obtained from this structure have high color saturation in the transitional region and a significantly gradual color change in the color changing region. The pigments of the present invention can be used as colored coatings, including printing ink, or can be used in the preparation of plastics, glass, ceramics and the like. The pigment of the present invention is particularly used in the cosmetic industry which has a very high requirement on gradual color change.

BRIEF DESCRIPTION OF THE DRAWINGS

FIG. 1b is linear scanning view of the components in the angle-dependent interference pigment sample of FIG. 1a;

FIG. 2b is an energy dispersive x-ray spectrum for the sample of FIG. 2a;

FIG. 3b is an energy dispersive x-ray spectrum for the sample of FIG. 3a.

DETAILED DESCRIPTION OF THE INVENTION

Example 1

Structure: sheet glass/mixture of ferric oxide and ferric silicate/silicon oxide/mixture of ferric oxide and ferric silicate 100 g of sheet glass (sodium calcium silicate) having a thickness of 2-3 micrometers and a particle diameter of 30-50 micrometers is obtained. Ferric trichloride or ferric sulfate solution is hydrolyzed on the surface of the sheet glass at a temperature of 80° C. and a pH of 4.0 to deposit a layer containing iron oxide hydroxides. Subsequently, sodium silicate solution is hydrolyzed at a temperature of 80° C. and a pH of 9 to deposit a silicon oxide hydroxides layer. Finally, ferric trichloride or ferric sulfate solution is again hydrolyzed at a temperature of 80° C. and a pH of 4.0 to deposit a second layer of iron oxide hydroxides. The thickness of respective layer (coating) is controlled by the addition amount of ferric salt solution and sodium silicate solution. The slurry is filtered, dried at 150° C. and then calcined at 700° C. for 1 hour. Due to the heat movement, the ferric ions disperse and penetrate into the silicon oxide hydroxides layer, and the silicate ions disperse and penetrate into the iron oxide hydroxides layer. Finally, ferric silicate congregates at and near the interface of the $Fe_2O_3$ layer and $SiO_2$ layer. The content of ferric silicate is highest at the interface and decreases gradually as a function of distance from the interface. Therefore, a structure of sheet glass/mixture of ferric oxide and ferric silicate/silicon oxide/ mixture of ferric oxide and ferric silicate is obtained, with the layer of mixture of ferric oxide and ferric silicate having high refractive index and the layer of silicon oxide having low refractive index.

The pigment prepared as above is mixed with a colorless and transparent adhesive made from nitrocellulose in a suitable ratio. The pigment shows very high color saturation and a color flow from fuchsia to yellow-green with very significantly gradual color change.

Figure 1A:
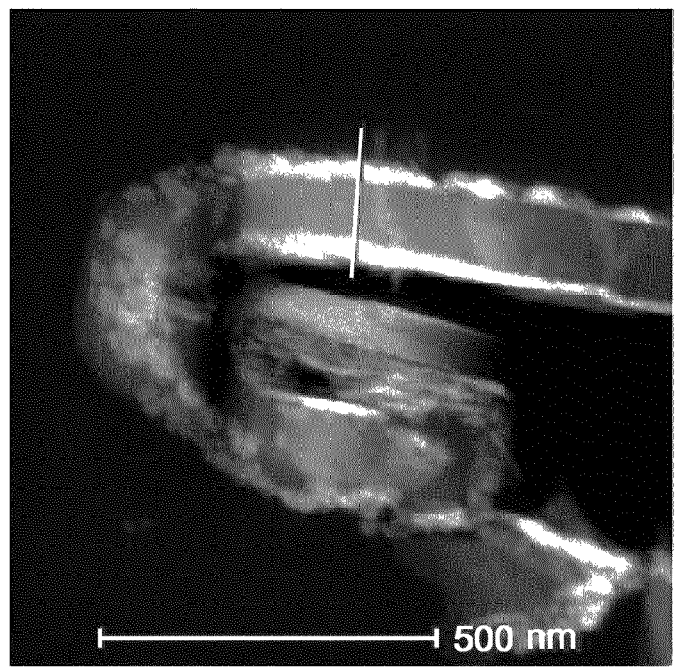
FIG. 1a is an SEM micrograph of the angle-dependent interference pigment sample obtained from Example 1 of the invention.
Figure 1B:
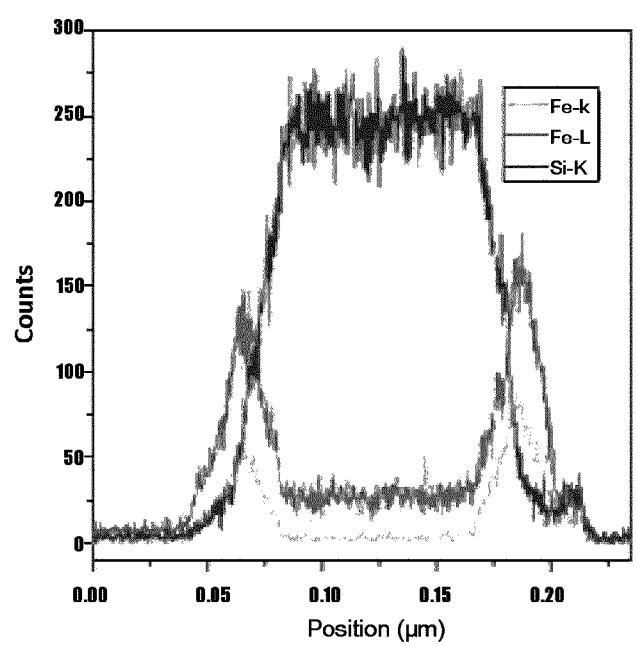
Figure 2A:
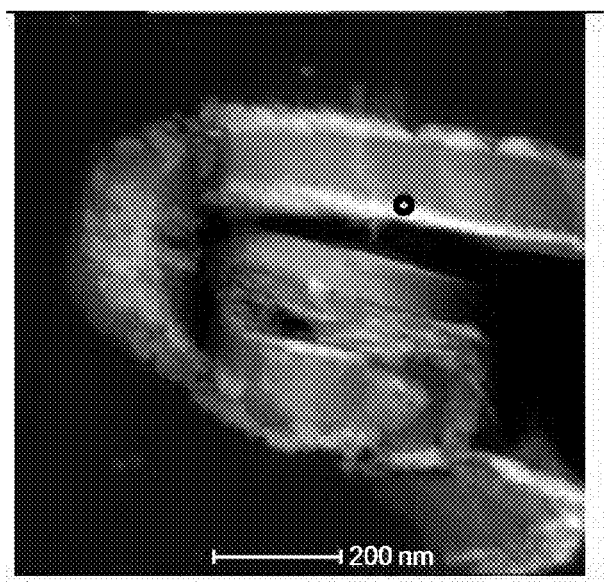
FIG. 2a is an SEM micrograph of another angle-dependent interference pigment sample obtained from Example 1.
Figure 2B:
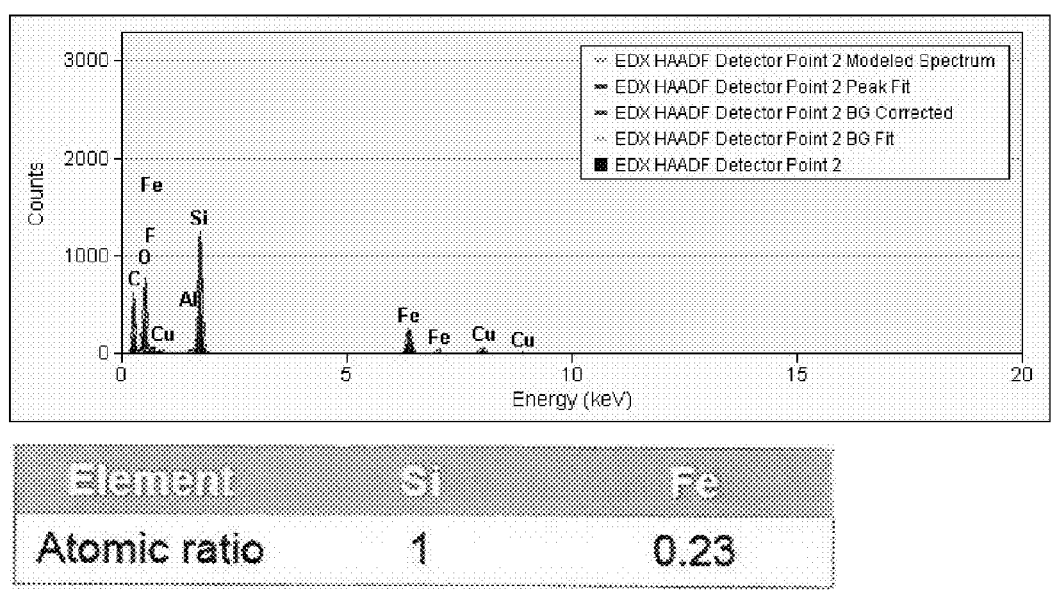
Figure 3A:
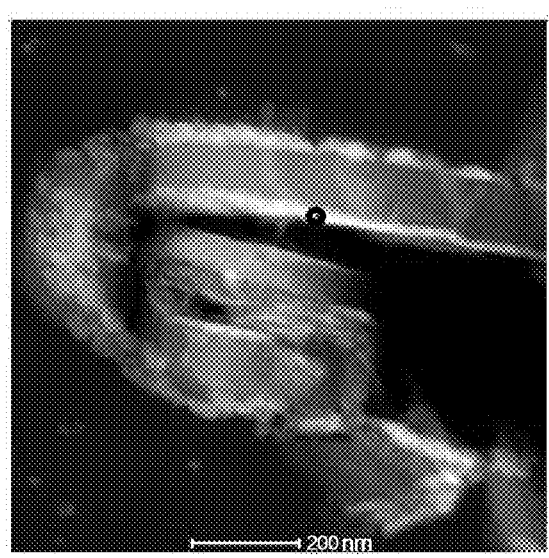
FIG. 3a is an SEM micrograph of a further angle-dependent interference pigment sample in Example 1.
Figure 3B:
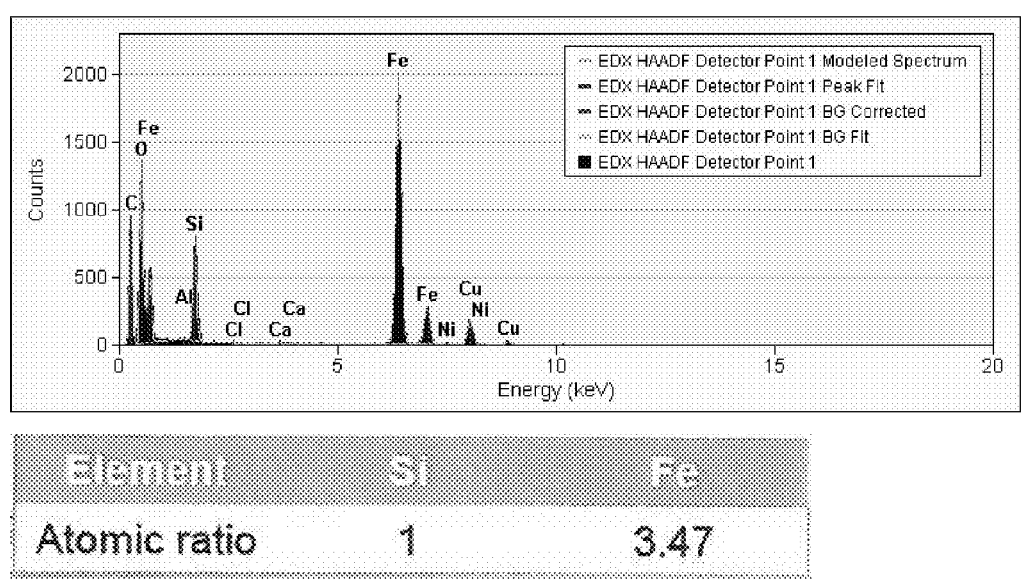

A SEM microscopy and linear scanning of the sample is performed, the results of which are shown in FIGS. 1a and 1b. As shown in the figures, two layers in the sample contain ferric silicate.

Ferric silicate can be expressed by a general formula "$Fe_{2-x}Si_{3x/4}O_3$". According to the spectrum shown in FIG. 1b, in the layer of mixture of ferric oxide and ferric silicate close to the sheet glass and the layer of mixture of ferric oxide and ferric silicate located outmost, the closer to the pure silicon oxide layer, the less the value of "x" is.

FIGS. 2a, 2b, 3a and 3b clearly show that the Si/Fe ratio in the layer of mixture of ferric oxide and ferric silicate varies. The Si/Fe ratio is 1:0.24 at a point close to the pure silicon oxide layer and 1:3.65 at a point close to the sheet glass. The refractive index of the two layer of mixture of ferric oxide and ferric silicate thus gradually changes, which is an important reason for the high color saturation and smooth color transition.

Example 2

Structure: muscovitize mica/mixture of titanium dioxide and titanium silicate or titanosilicate/silicon oxide/mixture of titanium dioxide and titanium silicate or titanosilicate 16 g of muscovitize mica powder having a particle diameter of 10-60 micrometers is obtained. Titanium tetrachloride solution is hydrolyzed on the surface of the muscovitize mica at a temperature of 75° C. and a pH of 2.5 to deposit a layer containing titanium dioxide hydroxides. Subsequently, sodium silicate solution is hydrolyzed at a temperature of 80° C. and a pH of 8.5 to deposit a silicon oxide hydroxides layer. Finally, titanium tetrachloride solution is hydrolyzed at a temperature of 75° C. and a pH of 2.5 to deposit a second layer of titanium dioxide hydroxides. The thickness of respective layer (coating) is controlled by the addition amount of titanium tetrachloride solution and sodium silicate solution. The slurry is filtered, dried at 150° C. and then calcined at 800° C. for 1 hour. Due to the heat movement, the titanium ions disperse and penetrate into the silicon oxide hydroxides layer, and the silicate ions disperse and penetrate into the titanium oxide hydroxides layer. Finally, titanium silicate or titanosilicate congregates at and near the interface of the $TiO_2$ layer and $SiO_2$ layer. Therefore, a structure of muscovitize mica/mixture of titanium dioxide and titanium silicate or titanosilicate/silicon oxide/mixture of titanium dioxide and titanium silicate or titanosilicate is obtained, with the layer of mixture of titanium dioxide and titanium silicate or titanosilicate having high refractive index and the layer of silicon oxide having low refractive index.

The pigment prepared as above is mixed with water soluble oxidized starch and adhesive agent made of PVA in a suitable ratio. The pigment shows very high color saturation and a color flow from bluish-green to orange-yellow with very significantly gradual color change.

Example 3

Structure: sheet glass/mixture of ferric oxide and ferric silicate/silicon oxide/mixture of ferric oxide and ferric silicate/mixture of aluminum oxide and silicon oxide The pigment prepared by example 1 is suspended in deionized water. Aluminum chloride solution is hydrolyzed on the surface of the pigment at a temperature of 75° C. and a pH of 5 to deposit an aluminum oxide hydroxides layer. The slurry is stirred for 15 min and adjusted to pH 8.5 using sodium hydroxide. To the slurry is added sodium silicate solution until a desired thickness is obtained. The slurry is filtered, dried and calcined to obtain a pigment with a structure of sheet glass/mixture of ferric oxide and ferric silicate/silicon oxide/mixture of ferric oxide and ferric silicate/mixture of aluminum oxide and silicon oxide. The thickness of the protective layer of mixture of aluminum oxide and silicon oxide can be controlled through the addition amount of the aluminum chloride solution and sodium silicate solution.

The pigment prepared as above is mixed with a colorless and transparent adhesive made from nitrocellulose in a suitable ratio. The pigment shows very high color saturation and a color flow from fuchsia to yellow-green with very significantly gradual color change. It can be seen that, when the protective layer is consisted of low refractive index materials, the interference color of the pigment is less affected.

Example 4

Structure: sheet glass/mixture of ferric oxide and ferric silicate/silicon oxide/mixture of ferric oxide and ferric silicate/silicon oxide/mixture of aluminum oxide and silicon oxide On the surface of the pigment prepared by example 1, sodium silicate solution is hydrolyzed at a temperature of 80° C. and a pH of 9 to deposit a silicon oxide hydroxides layer. Subsequently, ferric trichloride or ferric sulfate solution is hydrolyzed at a temperature of 80° C. and a pH of 4.0 to deposit a second layer of iron oxide hydroxides. The thickness of respective layer (coating) is controlled by the addition amount of ferric salt solution and sodium silicate solution. The slurry is filtered, dried at 150° C. and then calcined at 700° C. for 1 hour. A pigment with a structure of sheet glass/mixture of ferric oxide and ferric silicate/silicon oxide/ mixture of ferric oxide and ferric silicate/silicon oxide/mixture of aluminum oxide and silicon oxide is obtained.

The pigment prepared as above is mixed with a colorless and transparent adhesive made from nitrocellulose in a suitable ratio. The pigment shows higher color saturation and more smooth color transition.

Example 5

Structure: muscovitize mica/mixture of titanium dioxide and titanium silicate or titanosilicate/$SiO_2$/mixture of titanium dioxide and titanium silicate or titanosilicate/$SiO_2$/mixture of titanium dioxide and titanium silicate or titanosilicate On the surface of the pigment prepared by example 2, sodium silicate solution is hydrolyzed at a temperature of 80° C. and a pH of 8.5 to deposit a layer of silicon oxide hydroxides. Subsequently, a titanium tetrachloride solution is hydrolyzed at a temperature of 75° C. and a pH of 2.5 to deposit a second layer of titanium dioxide hydroxides. The thickness of respective layer (coating) is controlled by the addition amount of titanium tetrachloride solution and sodium silicate solution. The slurry is filtered, dried at 150° C. and then calcined at 800° C. for 1 hour. A pigment with a structure of muscovitize mica/mixture of titanium dioxide and titanium silicate or titanosilicate/$SiO_2$/mixture of titanium dioxide and titanium silicate or titanosilicate/$SiO_2$/mixture of titanium dioxide and titanium silicate or titanosilicate is obtained.

The pigment prepared as above is mixed with water soluble oxidized starch and adhesive agent made of PVA in a suitable ratio. The pigment shows higher color saturation and more smooth color transition.

The angle-dependent interference pigment of the present invention can be used with various types of other pigments, particularly transparent organic pigments, metal pigments or metal oxide pigments, so that various colors and optical effects can be obtained.

What is claimed is:

1. An angle-dependent interference pigment based on transparent or translucent inorganic flake serving as a substrate, the substrate being coated by at least one layer packet comprising in sequence by:

(A) a coating having high refractive index,
(B) a colorless coating having a refractive index n≤1.8,
(C) a coating having high refractive index, and optionally,
(D) an outer protective layer;

wherein the coating (B) is always between coating (A) and coating (C) so as to form a "high-low-high" refractive index layered structure, the "high-low-high" refractive index layered structure having an odd number of layers with the odd number being 3 or more; the coatings (A) and (C) consisting of metal oxides and silicate, and the silicate has its highest content at the interface between the coating with high refractive index and the coating with low refractive index and less content far from the interface; the coating (B) consisting of silicon oxide, hydrous silicon oxide, aluminum oxide, hydrous aluminum oxide, magnesium oxide, hydrous magnesium oxide and/or a mixture thereof.

2. The angle-dependent interference pigment of claim 1, wherein:

the coating (B) consisting of silicon oxide or a mixture of silicon oxide and hydrous silicon oxide.

3. The angle-dependent interference pigment of claim 1, wherein:
the thickness of the coating (B) is in the range of 20-1000 nm and preferably 50-900 nm.

4. The angle-dependent interference pigment of claim 1, wherein:
the thickness of the coatings (A) and (C) is respectively in the range of 5-165 nm and preferably 10-150 nm.

5. The angle-dependent interference pigment of claim 1, wherein:
the protective layer (D) consists of colorless or colored metal oxides, metal oxides hydroxides, nonmetal oxides, nonmetal oxides hydroxides and/or phosphates.

6. A coating which comprises a pigment according to the angle-dependent interference pigment of claim 1.

7. A paint which comprises a pigment according to the angle-dependent interference pigment of claim 1.

8. An ink which comprises a pigment according to the angle-dependent interference pigment of claim 1.

9. A plastic which comprises a pigment according to the angle-dependent interference pigment of claim 1.

10. A glass which comprises a pigment according to the angle-dependent interference pigment of claim 1.

11. A ceramic which comprises a pigment according to the angle-dependent interference pigment of claim 1.

12. A cosmetic which comprises a pigment according to the angle-dependent interference pigment of claim 1.

* * * * *